(12) United States Patent
Savva

(10) Patent No.: US 7,831,393 B2
(45) Date of Patent: Nov. 9, 2010

(54) METHODS AND PRODUCTS FOR ERROR DETERMINATION OF DRUG DOSE IN PHARMACEUTICAL MIXTURES

(75) Inventor: Michalakis Savva, Roselle Park, NJ (US)

(73) Assignee: Vagma, LLC, Roselle Park, NJ (US)

( * ) Notice: Subject to any disclaimer, the term of this patent is extended or adjusted under 35 U.S.C. 154(b) by 1118 days.

(21) Appl. No.: 11/465,633

(22) Filed: Aug. 18, 2006

(65) Prior Publication Data

US 2008/0046188 A1    Feb. 21, 2008

(51) Int. Cl.
*G01N 33/48* (2006.01)
(52) U.S. Cl. ....................................................... 702/19
(58) Field of Classification Search .................... 702/19
See application file for complete search history.

*Primary Examiner*—Jerry Lin
(74) *Attorney, Agent, or Firm*—Lucas & Mercanti, LLP

(57) ABSTRACT

The present invention discloses a computer program and a method including an algorithm for computing the uncertainty of drug concentration in pharmaceutical dosage forms. The invention also provides a computer system, a website and an IC chip incorporating the program product. The invention determines the allowable sensitivity of the instruments measuring each of the components and the least allowable weight (LAW) within a maximum allowable error of each ingredient at the predetermined assay standard. The method and products allow the accurate error evaluation of drug dose in pharmaceutical mixtures and unit dosage forms, which may be composed of an infinite number of ingredients that are measured on multiple equipments of variable sensitivities. Thus this invention provides instant guidance on the pharmaceutical ingredient preparation.

5 Claims, 7 Drawing Sheets

Type of error analysis    | Error associated with the finished product ▼ |

Choose number of components =    | 2 components ▼ |

Submit Query

4B

Input weight of finished product: | 0 | in gram ▼ |

Input sensitivity of balance used to measure final product: | 0 | in gram ▼ |

# 1 component

Input quantity of ingredient # 1: | 0 | in gram ▼ |

Input sensitivity of balance to measure # 1: | 0 | in gram ▼ |

# 2 component

Input quantity of ingredient # 2: | 0 | in gram ▼ |

Input sensitivity of balance to measure # 2: | 0 | in gram ▼ |

Submit Query

FIG. 5

| Weight of product | 0.25 |
|---|---|
| Sensitivity of balance for measuring product | 0.005 |
| Weight of ingredient # 1 | 0.07 |
| Sensitivity # 1 | 0.006 |
| Weight of ingredient # 2 | 2.73 |
| Sensitivity # 2 | 0.1 |
| | |
| Error associated with the finished product | 2 % |
| | | |
| Percent error associated with the drug in the mixture = | 3.57142857142857 | % |
| Overall error associated with the drug in the dosage form = | 5.57142857142857 | % |

METHODS AND PRODUCTS FOR ERROR DETERMINATION OF DRUG DOSE IN PHARMACEUTICAL MIXTURES

FIELD OF INVENTION

The present invention relates to a computer system and a program product for computing errors associated with the measurement and physical mixing of multiple pharmaceutical ingredients present as mixtures and more particularly it relates to an algorithm for calculating analytical errors for an infinite number of ingredients composing pharmaceutical mixtures measured with an infinite number of analytical instruments of same or variable sensitivity by using mathematics of Taylor series expansion.

BACKGROUND OF THE INVENTION

Quite frequently experimentally measured quantities have to be combined in some way in order to determine some other derived quantity. For example, in order to find the uncertainty in drug concentration of a drug that was measured on a balance of a particular sensitivity and mixed with excipients measured on a balance of same or different sensitivity, the uncertainties in the measured quantities have to be combined appropriately.

In the pharmaceutical industry, the Federal Drug Administration (FDA) approves only dosage forms in which the drug content conforms to the specified one with a very small allowable variation. A limited survey conducted by the Federal Drug Administration, Division of Drug Compliance and Surveillance, on compounded drug products in 2001, showed that 31% of the products failed a standard assay testing, with a range of 59 percent to 89 percent of expected potency.[1] In this same survey, the failure rate of commercial drug products was found to be close to 2%. The results of the survey are alarming and undoubtedly they jeopardize the future role of compounding pharmacy as an integral part of the country's modern healthcare system.

As shown in FIG. 1, manufacturers have to choose using whole stock mixture to manufacture excess pharmaceutical dosage forms or just an aliquot to yield exactly the desired quantity of unit dosage forms. Large scale pharmaceutical manufacturers would perhaps prefer route 1, while smaller scale GMP certified manufacturers would perhaps prefer the more economic route 2. The representative dosage form shown here is a tablet, but it could be any other pharmaceutical dosage form, i.e, capsule, powder, suppository, etc.

What we need to understand is that large scale manufactures mix ingredients at quantities large enough to produce thousands or millions of pharmaceutical unit dosage forms for individual patient use. Those ingredients that constitute the mixture or the formula, are measured separately on designated balances of certain sensitivity and subsequently mixed in large blenders for the purpose of producing homogeneous powder mixtures of uniform consistency throughout. Sometimes the whole quantity is used to produce unit dosage forms but sometimes only an aliquot of the stock mixture is used at a time. To correctly calculate the maximum potential error of the drug quantity in the unit dose or finished product one has to account for the error incurred in all measurements at all steps of the manufacturing process and combine these errors appropriately. Errors associated with the measurement of the individual ingredients composing the mixture can be calculated using error propagation theories, whereas errors associated with measurement of the powder mixture can be added together. The resultant overall error is dependent on the particular process used to manufacture the product, that is, use of the aliquot method or use of the whole powder mixture (FIG. 1, route 1 and 2, respectively).

It is important to understand the difference between type of analysis C and D from analysis E (see *Application of the Algorithm* in "Detailed Description of the Invention" section). The user may wish to use the whole powder mixture prepared to manufacture excess quantity of dosage forms or finished product. The user needs to use the Aliquot concept only if the intention is to produce the exact quantity of individual dosage forms as specified in the formula or prescription. Both methods are acceptable and they share certain advantages and disadvantages. For example, the advantage of the aliquot method is that the user may use the remaining of the stock powder to manufacture a different "strength" dosage forms or dosage forms of different composition. Large-scale manufactures usually prefer manufacturing excess product especially if they know that other orders for this product will arrive in the near future. This way, costly and cumbersome extra cleaning of equipments and rooms utilized to manufacture the particular dosage form is avoided. Another potential advantage of manufacturing excess dosage forms lies in the possible increased stability of the drug in the dosage form as compared to its stability in the bulk powder mixture.

There is currently no method available that determines the error of an ingredient concentration present in a mixture. The present invention relates to a novel approach that combines uncertainties in the measurements of drug and excipients and effectively calculates the maximum potential error of drug concentration in pharmaceutical mixtures.

SUMMARY OF INVENTION

This invention presents a novel program product and systems to determine, (1) the assay error associated with an ingredient in a mixture, (2) sensitivity requirement (SR) of a balance or any other analytical instrument with which ingredient quantity is determined, within a maximum allowable error (MAE), and (3) the Least allowable weight (LAW) or the Least Allowable Quantity (LAQ) within MAE for the ingredient concentrations in pharmaceutical dosage forms. The invention allows, in principle, determination of the error in drug dose, SR and LAQ as specified above, of any ingredient in a mixture composed of an infinite number of ingredients, which are measured or determined on multiple balances or other analytical instruments with variable sensitivities.

The invention provides a program product including a computer readable program encoded in a storage medium, said computer program executing an algorithm based on the equations 2, 2', 3 and/or 3' for determining variations of ingredient quantities in a mixture comprising steps of providing sensitivity requirement values of an instrument, executing the algorithm to determine the variations of the final concentration of the ingredient in a mixture, outputting said variation values for the comparison to a valid assay standard.

The invention also provides a method for determining variations of ingredient quantities in a mixture by using the program product The program product and the method of this invention can relate the sensitivities of measuring instruments to the variations of the final concentration of the ingredient in a mixture and generate plots or extrapolations of the value of sensitivities against the value of variations with respect to the predetermined number of measurements; or relate the sensitivities of measuring instruments to the amount of measurement of the ingredient for a mixture and generate plots or extrapolations of the value of sensitivities against the amount of measurement with respect to the predetermined variation standard, or relate the amount of measurement of the ingredient for a mixture to the variations of the final concentration of the ingredient in a mixture and generate plots or extrapolations of the amount of measurement against the variation values with respect to the predetermined sensitivities of measuring instruments.

The invention further provides a computer system incorporating the program product comprising input device for inputting required values, computing device for executing said algorithm, display/output device for display/output said plot or its extrapolation values.

The embodiments of the invention can also be a website incorporating the program product comprising first set of webpages for inputting required values, a server device storing and executing said algorithm, second set of webpages for displaying said plot or its extrapolation values.

The invention can also be embodied as a circuit chip incorporating the program product comprising an input outlet for inputting required values, a storage device for storing said program and its database, a computing device for executing the algorithm, an output outlet for output results.

BRIEF DESCRIPTION OF DRAWINGS

FIG. 4 4A. The screen setting for users' inquiry on the error associated with the measurement of an ingredient in a 2-component mixture. 4B. The screen setting for inputting values for product weight, ingredient quantities or sensitivities of the measuring instruments.

FIG. 5 The result of an error analysis of ingredient #1 in the 2-component final product.

DETAILED DESCRIPTION OF THE INVENTION

Figure 1:
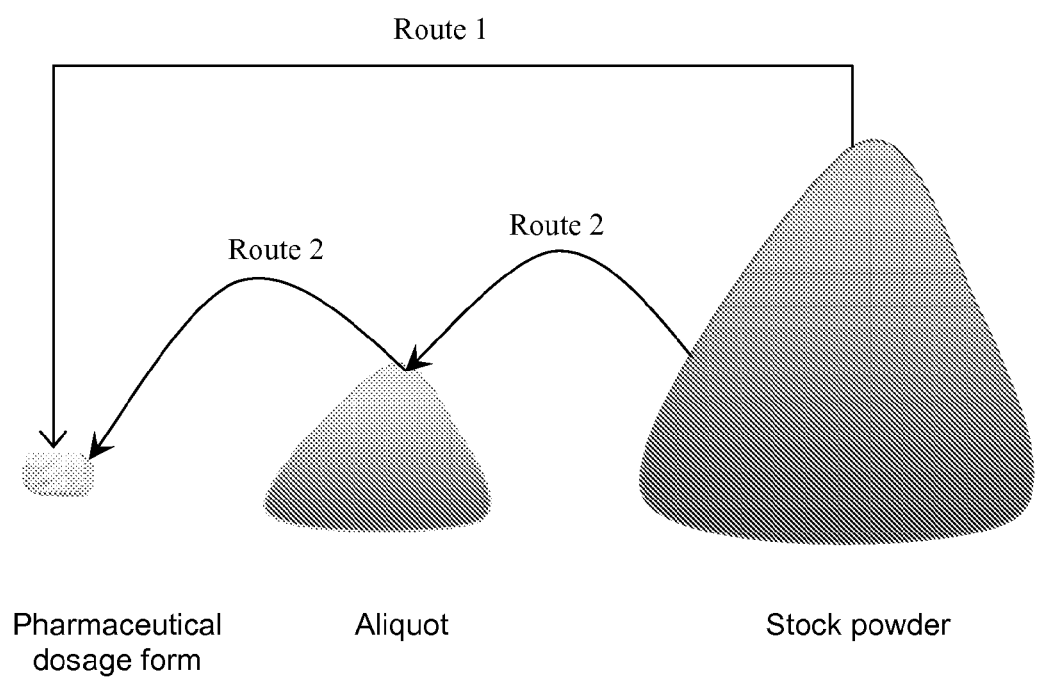
FIG. 1 Routs of preparing pharmaceutical ingredient for dosage formulation.

An object of the present invention is to provide an economical and effective program and computer system for determining assay errors of certain ingredients in a multi-component mixture.

The key idea in determining the error associated with drug dose in drug-excipient mixtures is to produce a function that describes the variation of the concentration of a ingredient in the whole mixture, as derived below:

$$f = \frac{x}{x+y+z+\ldots} \quad (1)$$

x=drug or ingredient quantity of interest y, z . . . =other ingredients f=concentration of a drug or ingredient of interest in the total mixture Equation 1) is continuous in the domain of our interest since x, y, z . . . are real positive numbers. The error associated with f can be found from the total differential of the function above, as shown below:

$$f = f(x, y, z, \ldots)$$

$$\Rightarrow df = \left|\frac{\partial f}{\partial x}\right|_{y,z,\ldots} dx + \left|\frac{\partial f}{\partial y}\right|_{x,z,\ldots} dy + \left|\frac{\partial f}{\partial z}\right|_{x,y,\ldots} dz + \ldots$$

Performing calculus of partial derivatives in equation 1, yields:

$$\Rightarrow df = \left|\frac{y+z+\ldots}{(x+y+z+\ldots)^2}\right| dx + \left|\frac{-x}{(x+y+z+\ldots)^2}\right| dy + \left|\frac{-x}{(x+y+z+\ldots)^2}\right| dz + \ldots \quad (2)$$

$$\Rightarrow \frac{df}{f} = \frac{y+z+\ldots}{x} \cdot \frac{dx}{(x+y+z+\ldots)} + \frac{dy+dz+\ldots}{(x+y+z+\ldots)} \quad (3)$$

Where dx, dy, dz are the absolute uncertainties associated with the measurement of the corresponding quantities x, y and z. More specifically, dx, dy, dz are equal to the sensitivity or readability of the balances utilized to measure the corresponding quantities x, y and z. df is the variation of the concentration of a interested ingredient with respect the whole composition, $$\frac{df}{f}$$

is the relative uncertainty in f, i.e., drug dosage error with respect to targeted drug concentration in the mixture.

Root-Sum-of-Squares (RSS) Method

Equation 2 could actually be modified to combine the standard deviations of each individual parameter to estimate the uncertainty in the results.

Let f=g(x, y, z, . . . )

Assuming that the most probable value of the two parameters are the mean values, $$\Rightarrow f(ave)=g(x(ave), y(ave), z(ave), \ldots))$$

The uncertainty in the value of z is, $$\sigma_f^2 = \lim(N \to \infty)\frac{1}{N}\sum (f_i - f(ave))^2$$

but $$f_i - f(ave) \cong$$

$$(x_i - x(ave))\left(\frac{\partial f}{\partial x}\right) + (y_i - y(ave))\left(\frac{\partial f}{\partial y}\right) + (z_i - z(ave))\left(\frac{\partial f}{\partial z}\right) + \ldots$$

$$\sigma_f^2 = \lim(N \to \infty)\frac{1}{N}\sum \left[(x_i - x(ave))\left(\frac{\partial f}{\partial x}\right) + (y_i - y(ave))\left(\frac{\partial f}{\partial y}\right) + (z_i - z(ave))\left(\frac{\partial f}{\partial z}\right) + \ldots\right]$$

$$\Rightarrow \sigma_f^2 \cong \sigma_x^2\left(\frac{\partial f}{\partial x}\right)^2 + \sigma_y^2\left(\frac{\partial f}{\partial y}\right)^2 + \sigma_z^2\left(\frac{\partial f}{\partial z}\right)^2 +$$

-continued $$2\sigma_{xy}^2\left(\frac{\partial f}{\partial x}\right)\cdot\left(\frac{\partial f}{\partial y}\right) 2\sigma_{xz}^2\left(\frac{\partial f}{\partial x}\right)\cdot\left(\frac{\partial f}{\partial z}\right) + 2\sigma_{zy}^2\left(\frac{\partial f}{\partial z}\right)\cdot\left(\frac{\partial f}{\partial y}\right) + \dots$$

The last three terms are expected to vanish in the limit of large random uncorrelated observations, therefore, $$\Rightarrow \sigma_f^2 \cong \sigma_x^2\left(\frac{\partial f}{\partial x}\right)^2 + \sigma_y^2\left(\frac{\partial f}{\partial y}\right)^2 + \sigma_z^2\left(\frac{f}{z}\right)^2 + \dots \quad (2')$$

$$\Rightarrow \sigma_f^2 = f^2\left[\left(\frac{y+z+\dots}{x}\right)^2 \cdot \frac{\sigma_x^2}{(x+y+z+\dots)^2} + \frac{\sigma_y^2 + \sigma_z^2 + \dots}{(x+y+z+\dots)^2}\right]$$

$$\Rightarrow \frac{\sigma_f}{f} = \left[\left(\frac{y+z+\dots}{x}\right)^2 \cdot \frac{\sigma_x^2}{(x+y+z+\dots)^2} + \frac{\sigma_y^2 + \sigma_z^2 + \dots}{(x+y+z+\dots)^2}\right]^{1/2} \quad (3')$$

Where, $$\frac{\sigma_f}{f}$$

is the relative uncertainty in f, i.e., drug dosage error with respect to the targeted drug concentration in the mixture.

Application of the Algorithm:

Equation 2, 2', 3 and/or 3' can be used in the following types of analysis to determine:

A. Error associated with the quantity of an ingredient present in a mixture
B. Sensitivity requirement (SR) of a balance within a maximum allowable error
C. Least allowable weight (LAW) of drug that can be measured within a maximum allowable error
D. All of the above (A, B, C) as related to the dosage form or finished product composed of the mixture
E. Type A, B and C analysis if the user plans to use only an aliquot from the final (or stock) powder mixture.

Program Product of this Invention

Figure 2:
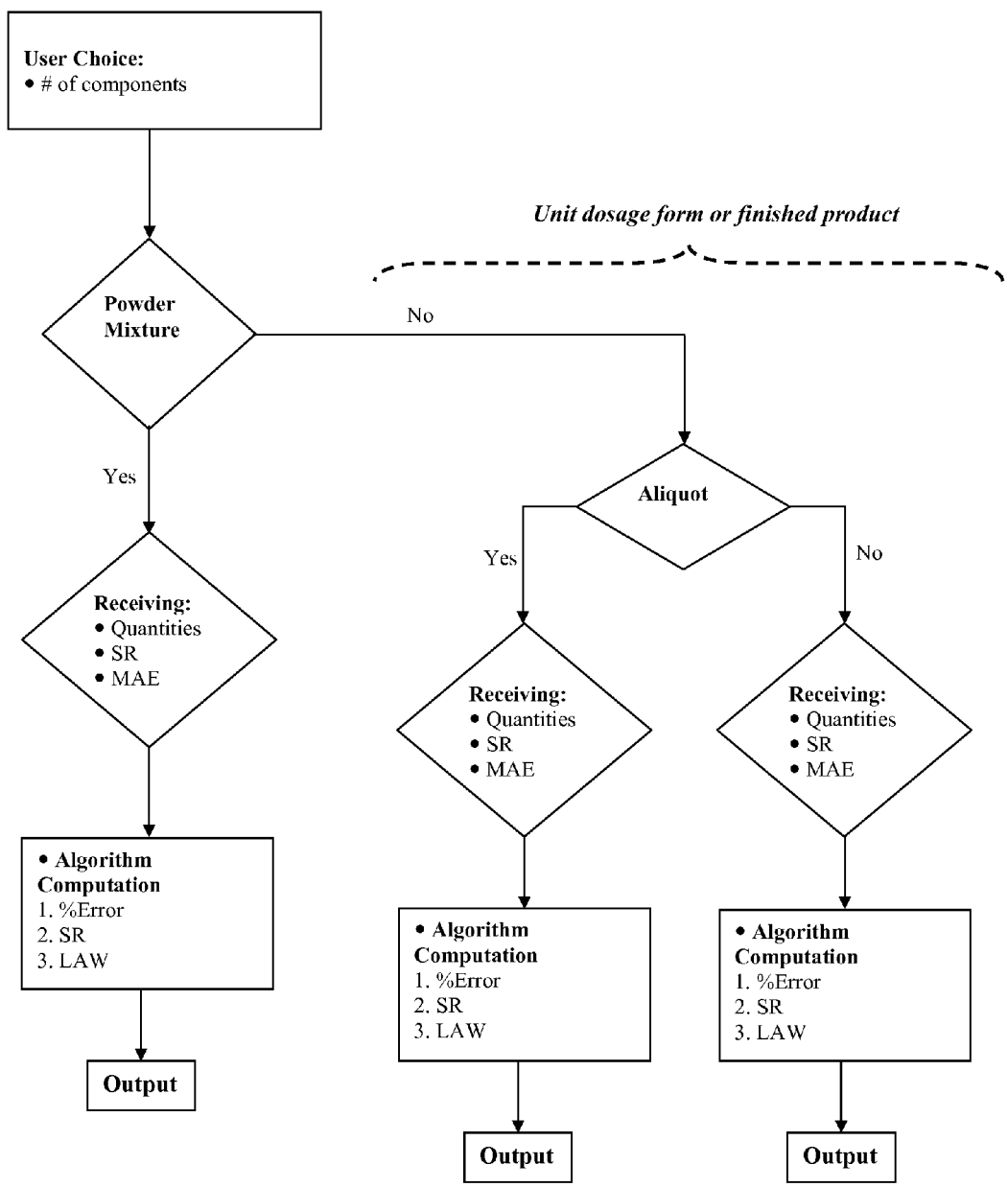
FIG. 2 A flow chart of the program product.
Figure 3:
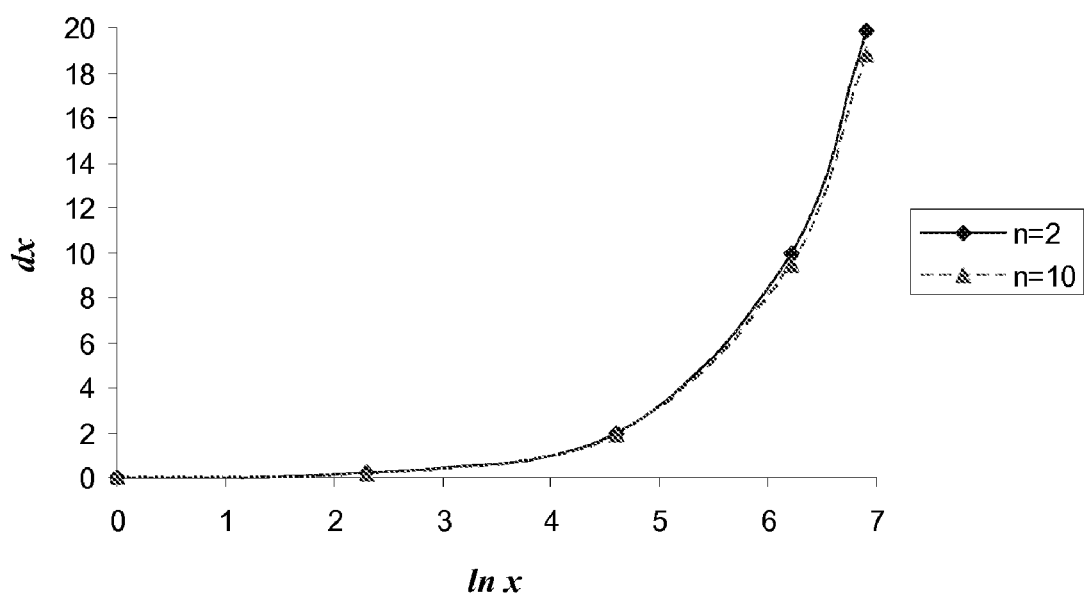
FIG. 3 A plot displays the variation of instrument sensitivity requirement (dx) with LAW of drug (x) within a 2% MAE in the dose, as a function of the number of measurements or ingredients composing the mixture (n)

A flow chart of the program product_that can be stored and run on all computers systems (PC or MAC) is provided in FIG. 2.

A Computer System of this Invention

Figure 6:
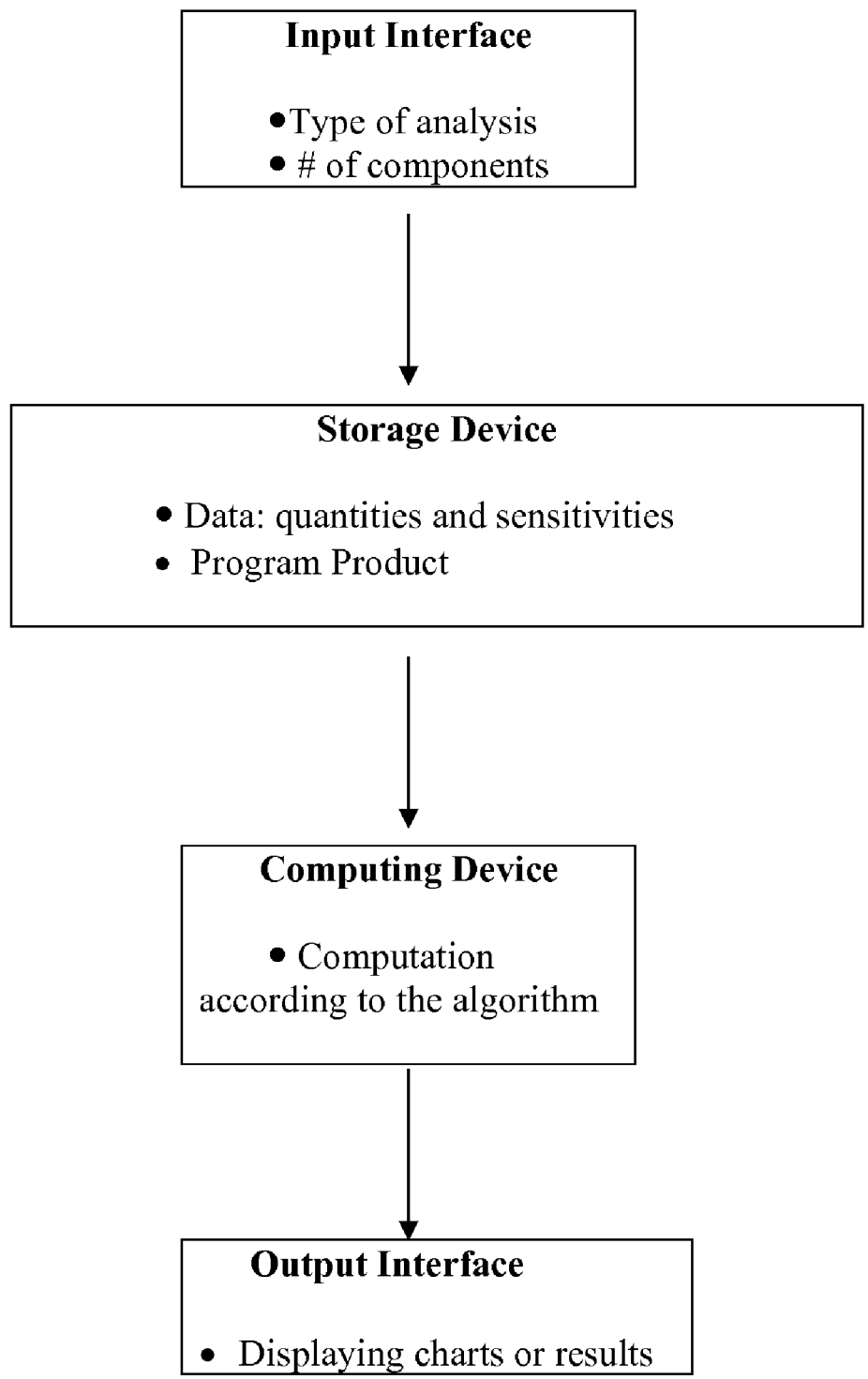
FIG. 6 A schematic chart for the computer system or an IC chip embodied the present invention.

The concept of a computer system embodiment of the invention is shown as a flow chart in FIG. 6.

A Website Embodiment of this Invention

Figure 7:
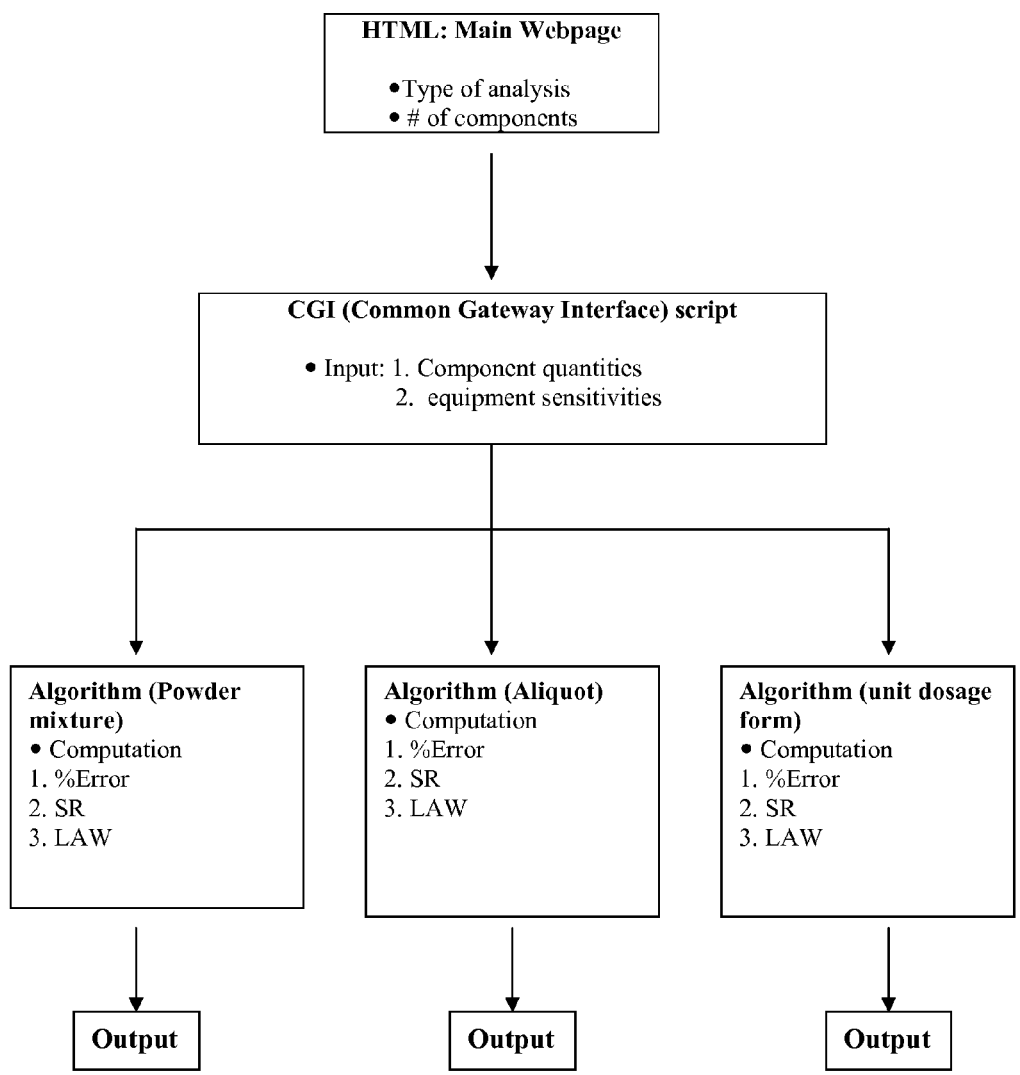
FIG. 7 A schematic chart for the Website embodied the present invention.

The concept of the website embodiment of the invention is shown in FIG. 7. A virtual demonstration of the program is shown as FIGS. 4-5. The "Error associated with an ingredient in a mixture" is chosen as the type of analysis for a mixture composed of 2 components.

The following examples are for the purpose of illustration. The one skilled in the art will readily appreciate that there are other applications and embodiments of the present invention. These examples should not be used to restrict the scope of this invention.

Example 1

Error Associated with an Ingredient in a Mixture for a Mixture Composed of 2 Components The operator is first asked to choose (a) the number of ingredients/components composing the mixture and (b) the type of error analysis. As in FIG. 4A, user can select a type of analysis from a list, such as, Error associated with the finished product, Sensitivity requirement within a maximum allowable error, or Least Allowable Weight within a maximum allowable error. In this case, "Error associated with the finished product" is selected. After submitting the Query, the user is asked to input all relevant quantities, in a form of a flow chart as shown below, in FIG. 4.

Given the following information/prescription:

| R | |
|---|---|
| Drug x | 0.5 g |
| Drug y | 2.5 g |
| Lactose, l | 67 g |

Mix and make 280 capsules

Aliquot, Capsules, drug x, drug y and lactose were measured on balances of readability, 1 g, 0.005 g, 0.01 g, 0.05 g and 1 g, respectively.

Based on the information above each capsule contains 250 mg of mixture. More specifically, the composition of each capsule is:

| Drug x | 1.786 mg |
|---|---|
| Drug y | 8.929 mg |
| Lactose, l | 239.286 mg |

In addition to the error associated with the measurement of each ingredient, errors associated with the measurement of the Aliquot and of the unit dosage form needs to be calculated, as well. MAE will be used to calculate the LAW of the particular ingredient of the mixture. The result is shown in FIG. 5 (in the unit of gram):

| Weight of product | 0.25 |
|---|---|
| Sensitivity of balance for measuring product | 0.005 |
| Weight of ingredient # 1 | 0.07 |
| Sensitivity # 1 | 0.006 |
| Weight of ingredient # 2 | 2.73 |
| Sensitivity # 2 | 0.1 |
| Error associated with the finished product | 2% |

Percent error associated with the drug in the mixture = 3.57142857142857%
Overall error associated with the drug in the dosage form = 5.57142857142857%

The following examples 2-4, demonstrate Computation of % Error of ingredient #1 in the unit dosage form, SR of the balance to measure ingredient #1 within a MAE equivalent to 8% and LAW of ingredient #1 to be measured within an 8% MAE, respectively.

Example 2

Determining the Uncertainty of the Drug Concentration in Unit Dosage Form or Finished Product Following the steps illustrated in Example 1: first making a selection for the analysis:

| Type of error analysis | Least allowable weight within a maximum allowable error |
|---|---|
| Choose # of components | 2 components |
| Submit Query | |

Then input the values for analysis:

| Input weight of finished product: | 0.250 in grams |
|---|---|
| Input sensitivity of balance used to measure final product: | 0.005 In gram |
| # 1 component | |
| Input quantity of ingredient # 1: | 0.07 in gram |
| # 2 component | |
| Input quantity of ingredient # 2: | 2.73 in gram |
| Input sensitivity of balance to measure # 2: | 0.1 in gram |
| Submit Query | |

After submit the query, the following result is provided:

| Weight of product | 0.25 g |
|---|---|
| Sensitivity of balance for measuring product | 0.005 g |
| Weight of ingredient # 1 | 0.07 g |
| Sensitivity # 1 | 0.006 g |
| Weight of ingredient # 2 | 2.73 g |
| Sensitivity # 2 | 0.1 g |
| Error associated with the finished product | 2% |
| Percent error associated with the drug in the mixture | 11.92857% |
| Overall error associated with the drug in the dosage form | 13.928571% |

Example 3

Determining the SR of the Balance that Needs to be Employed to Measure Ingredients within the Maximum Allowable Error of a Drug in the Finished Product

| Type of error analysis | Sensitivity requirement within a maximum allowable error |
|---|---|
| Choose # of components | 2 components |
| Submit Query | |

| Input Maximum Allowable Error: | 8% |
|---|---|
| Input weight of finished product: | 0.250 in grams |
| Input sensitivity of balance used to measure final product: | 0.005 In gram |
| # 1 component | |
| Input quantity of ingredient # 1: | 0.07 in gram |
| # 2 component | |
| Input quantity of ingredient # 2: | 2.73 in gram |
| Input sensitivity of balance to measure # 2: | 0.1 in gram |
| Submit Query | |

The analysis result is:

| Weight of product | 0.25 g |
|---|---|
| Sensitivity of balance for measuring product | 0.005 g |
| Weight of ingredient # 1 | 0.07 g |
| Weight of ingredient # 2 | 2.73 g |
| Sensitivity # 2 | 0.1 g |
| MAE associated with the finished product | 8% |
| Error associated with the measurement of finished product | 2% |
| Adjusted error associated with the drug in the final product | 6% |
| Sensitivity of the balance for drug measurement | 0.0017435 g |

Example 4

Calculating the LAW of an Ingredient in a Mixture Measured within a MAE

In this example, only an Aliquot equivalent to the amount of powder needed to manufacture the exact specified quantity of dosage forms will be used. The remaining powder will be stored for possible future use.

| Type of error analysis | Least allowable weight within a maximum allowable error |
|---|---|
| Choose # of components | 2 components |
| Submit Query | |

| Input Maximum Allowable Error: | 8% |
|---|---|
| Input weight of finished product: | 0.250 in grams |
| Input sensitivity of balance used to weigh the final product: | 0.005 in gram |
| Input Aliquot quantity | 1.25 in grams |
| Input sensitivity of balance used to weigh the Aliquot | 0.01 in grams |
| # 1 component | |
| Input quantity of ingredient # 1: | 0.07 in gram |
| Input sensitivity of balance to measure ingredient #1 | 0.006 in grams |
| # 2 component | |
| Input quantity of ingredient # 2: | 2.73 in gram |
| Input sensitivity of balance to measure # 2: | 0.1 in gram |
| Submit Query | |

After submitting the query, the following result is provided as follows:

| Weight of product | 0.25 g |
|---|---|
| Sensitivity of balance for measuring final product | 0.005 g |
| Weight of the Aliquot | 1.25 g |

-continued

| | |
|---|---|
| Sensitivity of balance for measuring the aliquot | 0.01 g |
| Sensitivity of the balance measured the ingredient #1 | 0.006 g |
| Sensitivity of the balance measured the ingredient # 2 | 0.1 g |
| MAE associated with the finished product | 8% |
| Adjusted error associated with the drug in the final product | 5.2% |
| The required least allowable weight of the ingredient #1 | 0.1606 g |
| The required least allowable weight of the ingredients | 6.2625 g |

REFERENCE

1. Statement by Galson, K. S., Acting Director of the Center for Drug Evaluation and Research, U.S. Food and Drug Administration, Department of Health and Human Services on Hearing: Federal and State Role in Pharmacy Compounding and Reconstitution: Exploring the Right Mix to Protect Patients, before the Senate Committee on Health, Education, Labor, and Pensions. Available at http://www.fda.gov/ola/2003/pharmacycompound1023.html. Accessed on Jan. 28, 2005.

I claim:

1. A program product for determining an error in an ingredient's quantities in a multi-component pharmaceutical formula measured by multiple analytical instruments, said error being a value of variation of concentration for a validation under an assay standard, the program product including a computer readable computer program encoded in a non-transitory tangible storage medium, said program product employing the steps of:

setting a computing mode according to a selection by a user on a type of error analysis;

receiving a value for a quantity of an ingredient of a composition to be measured by an instrument;

receiving a value for a sensitivity of the analytical instrument measuring the quantity of the ingredient;

repeating the two receiving steps for any remaining ingredients to be measured that compose the pharmaceutical formula;

executing an algorithm based on the following equations to relate: the quantities of measurements and sensitivities of instruments to a value of variation of the final concentration of any ingredient in the pharmaceutical formula:

$$df = \left|\frac{y+z+\ldots}{(x+y+z+\ldots)^2}\right|dx + \left|\frac{-x}{(x+y+z+\ldots)^2}\right|dy + \left|\frac{-x}{(x+y+z+\ldots)^2}\right|dz + \ldots$$

$$\sigma_f^2 \cong \sigma_x^2\left(\frac{\partial f}{\partial x}\right)^2 + \sigma_y^2\left(\frac{\partial f}{\partial y}\right)^2 + \sigma_z^2\left(\frac{f}{z}\right)^2 + \ldots$$

$$\frac{df}{f} = \frac{y+z+\ldots}{x} \cdot \frac{dx}{(x+y+z+\ldots)} + \frac{dy+dz+\ldots}{(x+y+z+\ldots)}$$

and/or $$\frac{\sigma_f}{f} = \left[\left(\frac{y+z+\ldots}{x}\right)^2 \cdot \frac{\sigma_x^2}{(x+y+z+\ldots)^2} + \frac{\sigma_y^2+\sigma_z^2+\ldots}{(x+y+z+\ldots)^2}\right]^{1/2}$$

where $df$ and $\sigma_f$ are an absolute variation of concentration of a ingredient in the pharmaceutical formula, $df/f$ and $\sigma_f/f$ are a relative variation of a dosage percentage of an ingredient in the pharmaceutical formula, x, y, z, . . . are quantities of ingredients of the dosage form, dx, dy, dz, . . . are sensitivities of the analytical instruments;

optionally plotting a relationship between quantities measurements of an ingredient, sensitivities of the instruments measuring the ingredient and a variation of a final concentration of the ingredient in a mixture in 2D or 3D chart; and outputting said value of variation of concentration for a validation under an assay standard as the error.

2. A method for determining the error in ingredient's quantities in a multi-component pharmaceutical formula measured by multiple analytical instruments by using the program product according to claim 1, said error corresponding to a value of variation of concentration for a validation under an assay standard, said program product being executed on hardware, the method comprising the steps of:

selecting a type of error analysis;

inputting a quantity value of an ingredient of a composition to be measured by an instrument;

inputting a sensitivity value of the analytical instrument measuring the quantity of the ingredient;

repeating the two inputting steps for any remaining ingredients to be measured that compose the pharmaceutical formula;

executing said program product to relate: the quantities of measurements and sensitivities of instruments to a value of variation of the final concentration of any ingredient in the pharmaceutical formula; and determining the value of variation according to an assay standard based on the plot or output values of variation.

3. A computer system incorporating the program product according to the claim 1, wherein said system comprises:

an input device for selecting a type of analysis and inputting the values of quantities and sensitivities;

a storage device storing the input values and said program product;

a computing device executing said program product on the input values; and an output device for displaying or outputting said value of variation.

4. A website incorporating the program product according to the claim 1, wherein said website comprises:

a first set of webpages for selecting a type of analysis and inputting the values of quantities and sensitivities;

a second set of webpages for displaying said values of variation; and a server device executing said program product and storing the two sets of webpages and said program product.

5. An IC chip incorporating the program product according to the claim 1, wherein said chip comprises:

an input interface for receiving the selection of a type of analysis and the values of quantities and sensitivities;

a storage device storing said program product and input values;

a computing device for executing said program product; and an output interface for outputting the values of variation.

* * * * *

UNITED STATES PATENT AND TRADEMARK OFFICE
CERTIFICATE OF CORRECTION

PATENT NO. : 7,831,393 B2
APPLICATION NO. : 11/465633
DATED : November 9, 2010
INVENTOR(S) : Michalakis Savva It is certified that error appears in the above-identified patent and that said Letters Patent is hereby corrected as shown below:

On column 4, line 31,
  please replace "the whole composition," with --the whole composition.--.

On column 4, lines 55-64,
  please replace the formula $$f_i - f(ave) \cong (x_i - x(ave))\left(\frac{\partial f}{\partial x}\right) + (y_i - y(ave))\left(\frac{\partial f}{\partial y}\right) + (z_i - z(ave))\left(\frac{\partial f}{\partial z}\right) + \ldots$$

$$\sigma_f^2 = \lim(N \to \infty)\frac{1}{N}\sum\left[(x_i - x(ave))\left(\frac{\partial f}{\partial x}\right) + (y_i - y(ave))\left(\frac{\partial f}{\partial y}\right) + (z_i - z(ave))\left(\frac{\partial f}{\partial z}\right) + \ldots\right]$$

" with $$f_i - f(ave) \cong (x_i - x(ave))\left(\frac{\partial f}{\partial x}\right) + (y_i - y(ave))\left(\frac{\partial f}{\partial y}\right) + (z_i - z(ave))\left(\frac{\partial f}{\partial z}\right) + \ldots$$

$$\sigma_f^2 = \lim(N \to \infty)\frac{1}{N}\sum\left[(x_i - x(ave))\left(\frac{\partial f}{\partial x}\right) + (y_i - y(ave))\left(\frac{\partial f}{\partial y}\right) + (z_i - z(ave))\left(\frac{\partial f}{\partial z}\right) + \ldots\right]^2$$

--.

On column 4, line 65 - column 5, line 5, please replace the formula $$\sigma_f^2 \cong \sigma_x^2\left(\frac{\partial f}{\partial x}\right)^2 + \sigma_y^2\left(\frac{\partial f}{\partial y}\right)^2 + \sigma_z^2\left(\frac{\partial f}{\partial z}\right)^2 + 2\sigma_{xy}^2\left(\frac{\partial f}{\partial x}\right)\cdot\left(\frac{\partial f}{\partial y}\right) +$$

$$2\sigma_{xz}^2\left(\frac{\partial f}{\partial x}\right)\cdot\left(\frac{\partial f}{\partial z}\right) 2\sigma_{zy}^2\left(\frac{\partial f}{\partial z}\right)\cdot\left(\frac{\partial f}{\partial y}\right) + \ldots$$

" with

Signed and Sealed this
Twenty-fifth Day of January, 2011

David J. Kappos
*Director of the United States Patent and Trademark Office*

CERTIFICATE OF CORRECTION (continued)
U.S. Pat. No. 7,831,393 B2

$$\Rightarrow \quad \sigma_f^2 \cong \sigma_x^2\left(\frac{\partial f}{\partial x}\right)^2 + \sigma_y^2\left(\frac{\partial f}{\partial y}\right)^2 + \sigma_z^2\left(\frac{\partial f}{\partial z}\right)^2 + 2\sigma_{xy}^2\left(\frac{\partial f}{\partial x}\right)\cdot\left(\frac{\partial f}{\partial y}\right) +$$

$$2\sigma_{xz}^2\left(\frac{\partial f}{\partial x}\right)\cdot\left(\frac{\partial f}{\partial z}\right) + 2\sigma_{zy}^2\left(\frac{\partial f}{\partial z}\right)\cdot\left(\frac{\partial f}{\partial y}\right) + \ldots$$

-- --.

On column 5, line 49,
  please replace "the program product_that can be stored" with --the program product that can be stored--.

On column 5, lines 10-20,
  please replace the formula $$\Rightarrow \quad \sigma_f^2 \cong \sigma_x^2\left(\frac{\partial f}{\partial x}\right)^2 + \sigma_y^2\left(\frac{\partial f}{\partial y}\right)^2 + \sigma_z^2\left(\frac{\partial f}{\partial z}\right)^2 + \ldots$$

$$\Rightarrow \quad \sigma_f^2 = f^2\left[\left(\frac{y+z+\ldots}{x}\right)^2 \cdot \frac{\sigma_x^2}{(x+y+z+\ldots)^2} + \frac{\sigma_y^2 + \sigma_z^2 + \ldots}{(x+y+z+\ldots)^2}\right] \quad (2')$$

$$\Rightarrow \quad \frac{\sigma_f}{f} = \left[\left(\frac{y+z+\ldots}{x}\right)^2 \cdot \frac{\sigma_x^2}{(x+y+z+\ldots)^2} + \frac{\sigma_y^2 + \sigma_z^2 + \ldots}{(x+y+z+\ldots)^2}\right]^{1/2} \quad (3')"$$

with $$\Rightarrow \quad \sigma_f^2 \cong \sigma_x^2\left(\frac{\partial f}{\partial x}\right)^2 + \sigma_y^2\left(\frac{\partial f}{\partial y}\right)^2 + \sigma_z^2\left(\frac{\partial f}{\partial z}\right)^2 + \ldots$$

$$\Rightarrow \quad \sigma_f^2 = f^2\left[\left(\frac{y+z+\ldots}{x}\right)^2 \cdot \frac{\sigma_x^2}{(x+y+z+\ldots)^2} + \frac{\sigma_y^2 + \sigma_z^2 + \ldots}{(x+y+z+\ldots)^2}\right] \quad (2')$$

$$\Rightarrow \quad \frac{\sigma_f}{f} = \left[\left(\frac{y+z+\ldots}{x}\right)^2 \cdot \frac{\sigma_x^2}{(x+y+z+\ldots)^2} + \frac{\sigma_y^2 + \sigma_z^2 + \ldots}{(x+y+z+\ldots)^2}\right]^{1/2} \quad (3')$$

--.